(12) United States Patent
Schellenberger et al.

(10) Patent No.: US 10,195,579 B2
(45) Date of Patent: *Feb. 5, 2019

(54) MULTI-THROUGH HOLE TESTING PLATE FOR HIGH THROUGHPUT SCREENING

(71) Applicant: LIFE TECHNOLOGIES CORPORATION, Carlsbad, CA (US)

(72) Inventors: Volker Schellenberger, Palo Alto, CA (US); Amy Liu, Mountain View, CA (US)

(73) Assignee: Life Technologies Corporation, Carlsbad, CA (US)

( * ) Notice: Subject to any disclaimer, the term of this patent is extended or adjusted under 35 U.S.C. 154(b) by 304 days.

This patent is subject to a terminal disclaimer.

(21) Appl. No.: 14/873,005

(22) Filed: Oct. 1, 2015

(65) Prior Publication Data

US 2016/0089649 A1 Mar. 31, 2016

Related U.S. Application Data

(60) Continuation of application No. 13/276,179, filed on Oct. 18, 2011, which is a continuation of application
(Continued)

(51) Int. Cl.
*B01L 3/00* (2006.01)
*B01J 19/00* (2006.01)
(Continued)

(52) U.S. Cl.
CPC ......... *B01J 19/0046* (2013.01); *B01L 3/5025* (2013.01); *B01L 3/5085* (2013.01);
(Continued)

(58) Field of Classification Search
CPC .............. B01J 19/0046; B01J 19/00596; B01J 2219/00533; B01J 2219/00707;
(Continued)

(56) References Cited

U.S. PATENT DOCUMENTS 1,236,137 A 8/1917 Bastow
2,745,001 A 5/1956 Guth
(Continued)

FOREIGN PATENT DOCUMENTS

DE 10046224 3/2002
EP 0236069 9/1987
(Continued)

OTHER PUBLICATIONS

"Rev. Geophys", vol. 33 Suppl., (C) 1995 American Geophysical Union (Abstract Only).
(Continued)

*Primary Examiner* — Jill A Warden
*Assistant Examiner* — Dwayne K Handy

(57) ABSTRACT

A method for holding samples for analysis and an apparatus thereof includes a testing plate with a pair of opposing surfaces and a plurality of holes. Each of the holes extends from one of the opposing surfaces to the other one of the opposing surfaces. The holes are arranged in groups, where each group has at least two rows and two columns of holes. The groups are arranged in sets, where each set has at least two rows and two columns of groups. To analyze samples, at least one of the opposing surfaces of the testing plate is immersed in a solution to be analyzed. A portion of the solution enters openings for each of the holes in the immersed opposing surface. Once the holes are filled with solution, the testing plate is removed and is held above a supporting surface. Surface tension holds the solution in each of the holes. The solution in one or more of the holes is then analyzed and the solution in one of these holes is identified for further study. The location of the identified solution is marked based upon its location within a particular set and group of holes.

18 Claims, 6 Drawing Sheets

Related U.S. Application Data

No. 10/969,104, filed on Oct. 20, 2004, now abandoned, which is a division of application No. 10/223,893, filed on Aug. 20, 2002, now Pat. No. 7,666,360, which is a continuation of application No. 09/970,578, filed on Oct. 4, 2001, now Pat. No. 6,436,632, which is a continuation of application No. 09/528,085, filed on Mar. 17, 2000, now Pat. No. 6,306,578, which is a continuation-in-part of application No. 09/471,852, filed on Dec. 23, 1999, now abandoned, which is a continuation of application No. 09/272,122, filed on Mar. 19, 1999, now Pat. No. 6,027,873.

(51) Int. Cl.
   *C40B 60/14* (2006.01)
   *G01N 35/10* (2006.01)
   *G01N 35/00* (2006.01)

(52) U.S. Cl.
   CPC ... *B01L 3/50857* (2013.01); *B01J 2219/0052* (2013.01); *B01J 2219/00286* (2013.01); *B01J 2219/00317* (2013.01); *B01J 2219/00319* (2013.01); *B01J 2219/00524* (2013.01); *B01J 2219/00533* (2013.01); *B01J 2219/00596* (2013.01); *B01J 2219/00644* (2013.01); *B01J 2219/00659* (2013.01); *B01J 2219/00662* (2013.01); *B01J 2219/00707* (2013.01); *B01L 2300/0654* (2013.01); *B01L 2300/0809* (2013.01); *B01L 2300/161* (2013.01); *C40B 60/14* (2013.01); *G01N 35/1065* (2013.01); *G01N 2035/00237* (2013.01)

(58) Field of Classification Search
   CPC .... B01J 2219/00662; B01J 2219/00659; B01J 2219/0052; B01J 2219/00319; B01J 2219/00317; B01J 2219/00286; B01J 2219/00524; B01L 3/5085; B01L 3/5052; B01L 3/50857; B01L 2300/161; B01L 2300/0654; B01L 2300/0809; C40B 60/14; G01N 2035/00237; G01N 35/1065
   See application file for complete search history.

(56) References Cited

U.S. PATENT DOCUMENTS

| | | |
|---|---|---|
| 2,771,398 A | 11/1956 | Snyder |
| 3,043,669 A | 7/1962 | Charles |
| 3,170,980 A | 2/1965 | Pritchard |
| 3,252,331 A | 5/1966 | Lancaster |
| 3,768,974 A | 10/1973 | Storm |
| 3,770,383 A | 11/1973 | Price |
| 3,873,268 A | 3/1975 | McKie |
| 3,894,512 A | 7/1975 | Ohno |
| 4,007,010 A | 2/1977 | Woodbridge et al. |
| 4,065,263 A | 12/1977 | Woodbridge |
| 4,088,448 A | 5/1978 | Lilja et al. |
| 4,110,165 A | 8/1978 | Cole et al. |
| 4,111,754 A | 9/1978 | Park |
| 4,234,316 A | 11/1980 | Hevey |
| 4,273,877 A | 6/1981 | Anagnostopoulos |
| 4,415,732 A | 11/1983 | Caruthers et al. |
| 4,446,239 A | 5/1984 | Tsuji |
| 4,453,805 A | 6/1984 | Ashkin et al. |
| 4,458,066 A | 7/1984 | Caruthers et al. |
| 4,493,815 A | 1/1985 | Fernwood et al. |
| 4,500,707 A | 2/1985 | Caruthers et al. |
| 4,562,045 A | 12/1985 | Murata |
| 4,562,871 A | 1/1986 | Astle |
| 4,613,573 A | 9/1986 | Shibayama et al. |
| 4,626,509 A | 12/1986 | Lyman |
| 4,682,890 A | 7/1987 | de Macario et al. |
| 4,683,195 A | 7/1987 | Mullis et al. |
| 4,683,202 A | 7/1987 | Mullis |
| 4,734,192 A | 3/1988 | Champion et al. |
| 4,761,378 A | 8/1988 | Godsey |
| 4,828,386 A | 5/1989 | Matkovich et al. |
| 4,834,946 A | 5/1989 | Levin |
| 4,861,448 A | 8/1989 | Cantor et al. |
| 4,861,722 A | 8/1989 | Sano et al. |
| 4,893,886 A | 1/1990 | Ashkin et al. |
| 4,902,481 A * | 2/1990 | Clark .............. B01D 61/18 210/335 |
| 4,932,806 A | 6/1990 | Eklund et al. |
| 4,965,188 A | 10/1990 | Mullis et al. |
| 4,973,679 A | 11/1990 | Caruthers et al. |
| 4,990,459 A | 2/1991 | Maeda et al. |
| 5,000,921 A | 3/1991 | Hanaway et al. |
| 5,009,846 A | 4/1991 | Gavet et al. |
| 5,038,852 A | 8/1991 | Johnson et al. |
| 5,047,215 A | 9/1991 | Manns |
| 5,100,627 A | 3/1992 | Buican et al. |
| 5,108,704 A | 4/1992 | Bowers et al. |
| 5,108,926 A | 4/1992 | Klebe |
| 5,153,319 A | 10/1992 | Caruthers et al. |
| 5,192,980 A | 3/1993 | Dixon et al. |
| 5,210,021 A | 5/1993 | Goodwin, Jr. et al. |
| 5,215,593 A | 6/1993 | Nojo et al. |
| 5,219,727 A | 6/1993 | Wang et al. |
| 5,229,163 A | 7/1993 | Fox |
| 5,234,665 A | 8/1993 | Ohta et al. |
| 5,234,666 A | 8/1993 | Suzuki et al. |
| 5,262,128 A | 11/1993 | Leighton et al. |
| 5,284,753 A | 2/1994 | Goodwin, Jr. |
| 5,290,705 A | 3/1994 | Davis |
| 5,310,652 A | 5/1994 | Gelfand et al. |
| 5,322,770 A | 6/1994 | Gelfand |
| 5,333,675 A | 8/1994 | Mullis et al. |
| 5,366,088 A * | 11/1994 | Hill .............. B01L 9/543 206/443 |
| 5,374,525 A | 12/1994 | Lalouel et al. |
| 5,382,985 A | 1/1995 | Becker et al. |
| 5,407,800 A | 4/1995 | Gelfand et al. |
| 5,411,876 A | 5/1995 | Bloch et al. |
| 5,445,934 A | 8/1995 | Fodor et al. |
| 5,453,252 A | 9/1995 | Truett |
| 5,455,008 A | 10/1995 | Earley et al. |
| 5,466,583 A | 11/1995 | Thomson et al. |
| 5,475,610 A | 12/1995 | Atwood et al. |
| 5,476,774 A | 12/1995 | Wang et al. |
| 5,492,806 A | 2/1996 | Drmanac et al. |
| 5,504,007 A | 4/1996 | Haynes |
| 5,506,141 A | 4/1996 | Weinreb et al. |
| 5,508,197 A | 4/1996 | Hansen et al. |
| 5,508,200 A | 4/1996 | Tiffany et al. |
| 5,510,270 A | 4/1996 | Fodor et al. |
| 5,519,218 A | 5/1996 | Chang |
| 5,525,464 A | 6/1996 | Drmanac et al. |
| 5,538,848 A | 7/1996 | Livak et al. |
| 5,554,339 A | 9/1996 | Cozzette et al. |
| 5,560,811 A | 10/1996 | Briggs et al. |
| 5,561,058 A | 10/1996 | Gelfand et al. |
| 5,561,071 A | 10/1996 | Hollenberg et al. |
| 5,593,839 A | 1/1997 | Hubbell et al. |
| 5,599,664 A | 2/1997 | Schwartz |
| 5,602,756 A | 2/1997 | Atwood et al. |
| 5,605,662 A | 2/1997 | Heller et al. |
| 5,609,828 A | 3/1997 | O'Bear et al. |
| 5,621,094 A | 4/1997 | Roser et al. |
| 5,632,957 A | 5/1997 | Heller et al. |
| 5,641,391 A | 6/1997 | Hunter et al. |
| 5,641,864 A | 6/1997 | Gelfand |
| 5,656,493 A | 8/1997 | Mullis et al. |
| 5,667,972 A | 9/1997 | Drmanac et al. |
| 5,670,329 A | 9/1997 | Oberhardt |
| 5,744,101 A | 4/1998 | Fodor et al. |
| 5,759,779 A | 6/1998 | Dehlinger |
| 5,763,263 A * | 6/1998 | Dehlinger .......... B01J 19/0046 435/6.12 |
| 5,770,440 A | 6/1998 | Berndt |
| 5,770,860 A | 6/1998 | Franzen |

(56) References Cited

U.S. PATENT DOCUMENTS

| | | |
|---|---|---|
| 5,773,238 A | 6/1998 | Shukla |
| 5,780,233 A | 7/1998 | Guo et al. |
| 5,785,926 A | 7/1998 | Seubert et al. |
| 5,786,226 A | 7/1998 | Bocker et al. |
| 5,795,748 A | 8/1998 | Cottingham et al. |
| 5,807,522 A | 9/1998 | Brown et al. |
| 5,720,923 A | 10/1998 | Haff et al. |
| 5,840,862 A | 11/1998 | Bensimon et al. |
| 5,843,767 A | 12/1998 | Beattie et al. |
| 5,849,598 A | 12/1998 | Wilson et al. |
| 5,856,100 A | 1/1999 | Hayashizaki |
| 5,871,908 A | 2/1999 | Henco et al. |
| 5,879,632 A | 3/1999 | Demers |
| 5,888,723 A | 3/1999 | Sutton et al. |
| 5,897,842 A | 4/1999 | Dunn et al. |
| 5,910,287 A | 6/1999 | Cassin et al. |
| 5,922,604 A | 7/1999 | Stapleton et al. |
| 5,928,907 A | 7/1999 | Woudenberg et al. |
| 5,929,208 A | 7/1999 | Heller et al. |
| 5,942,432 A | 8/1999 | Smith et al. |
| 5,944,652 A | 8/1999 | Miller et al. |
| 5,955,377 A | 9/1999 | Maul et al. |
| 5,958,345 A | 9/1999 | Turner et al. |
| 5,962,316 A | 10/1999 | Beach et al. |
| 5,985,214 A | 11/1999 | Stylli et al. |
| 5,994,056 A | 11/1999 | Higuchi |
| 6,001,586 A | 12/1999 | Schellenberger |
| 6,004,744 A | 12/1999 | Goelet et al. |
| 6,020,141 A | 2/2000 | Pantoliano et al. |
| 6,024,925 A | 2/2000 | Little et al. |
| 6,027,873 A | 2/2000 | Schellenberger et al. |
| 6,060,240 A | 5/2000 | Kamb et al. |
| 6,071,702 A | 6/2000 | Yamamoto et al. |
| 6,071,748 A | 6/2000 | Modlin et al. |
| 6,083,763 A | 7/2000 | Balch |
| 6,086,825 A | 7/2000 | Sundberg et al. |
| 6,088,100 A | 7/2000 | Brenan et al. |
| 6,090,251 A | 7/2000 | Sundberg et al. |
| 6,103,199 A | 8/2000 | Bjornson et al. |
| 6,121,048 A | 9/2000 | Zaffaroni et al. |
| 6,136,566 A | 10/2000 | Sands et al. |
| H1919 H | 11/2000 | Caspar et al. |
| 6,143,496 A | 11/2000 | Brown et al. |
| 6,147,198 A | 11/2000 | Schwartz |
| 6,149,815 A | 11/2000 | Sauter |
| 6,174,670 B1 | 1/2001 | Wittwer et al. |
| 6,197,563 B1 | 3/2001 | Erlich et al. |
| 6,235,473 B1 | 5/2001 | Friedman et al. |
| 6,245,505 B1 | 6/2001 | Todd et al. |
| 6,251,343 B1 | 6/2001 | Dubrow et al. |
| 6,271,024 B1 | 8/2001 | Sve et al. |
| 6,284,113 B1 | 9/2001 | Bjornson et al. |
| 6,296,702 B1 | 10/2001 | Bryning et al. |
| 6,306,578 B1 | 10/2001 | Schellenberger et al. |
| 6,309,600 B1 | 10/2001 | Hunter et al. |
| 6,309,828 B1 | 10/2001 | Schleifer et al. |
| 6,312,103 B1 | 11/2001 | Haluzak |
| 6,337,435 B1 | 1/2002 | Chu et al. |
| 6,353,774 B1 | 3/2002 | Goldenberg et al. |
| 6,376,256 B1 | 4/2002 | Dunnington et al. |
| 6,387,331 B1 | 5/2002 | Hunter |
| 6,391,559 B1 | 5/2002 | Brown et al. |
| 6,399,396 B1 | 6/2002 | Bass |
| 6,399,952 B1 | 6/2002 | Maher et al. |
| 6,404,166 B1 | 6/2002 | Puchianu |
| 6,410,331 B1 | 6/2002 | Schultz et al. |
| 6,436,632 B2 | 8/2002 | Schellenberger et al. |
| 6,454,924 B2 | 9/2002 | Jedrzejewski et al. |
| 6,485,690 B1 | 11/2002 | Pfost et al. |
| 6,485,944 B1 | 11/2002 | Church et al. |
| 6,495,104 B1 | 12/2002 | Unno et al. |
| 6,496,369 B2 | 12/2002 | Nakamura |
| 6,503,757 B1 | 1/2003 | Chow |
| 6,544,737 B1 | 4/2003 | Blumenfeld et al. |
| 6,565,813 B1 | 5/2003 | Garyantes |
| 6,572,828 B1 | 6/2003 | Potyrailo et al. |
| 6,579,358 B2 | 6/2003 | Delucas et al. |
| 6,582,914 B1 | 6/2003 | Caldwell et al. |
| 6,638,761 B2 | 10/2003 | Shin et al. |
| 6,642,000 B1 | 11/2003 | Strizhkov et al. |
| 6,649,402 B2 | 11/2003 | Van der Weide et al. |
| 6,664,044 B1 | 12/2003 | Sato |
| 6,677,151 B2 | 1/2004 | Sandell |
| 6,682,702 B2 | 1/2004 | Barth et al. |
| 6,689,323 B2 | 2/2004 | Fisher et al. |
| 6,703,236 B2 | 3/2004 | Atwood |
| 6,706,538 B1 | 3/2004 | Karg et al. |
| 6,713,309 B1 | 3/2004 | Anderson et al. |
| 6,737,026 B1 | 5/2004 | Bergh et al. |
| 6,743,633 B1 | 6/2004 | Hunter |
| 6,821,486 B1 | 11/2004 | Akporiaye et al. |
| 6,827,831 B1 | 12/2004 | Chow et al. |
| 6,893,877 B2 | 5/2005 | Hunter et al. |
| 7,133,726 B1 | 11/2006 | Atwood et al. |
| 7,332,271 B2 | 2/2008 | O'Keefe et al. |
| 7,390,457 B2 | 6/2008 | Schembri |
| 7,666,360 B2 | 2/2010 | Schellenberger et al. |
| 2001/0046702 A1 | 11/2001 | Schembri |
| 2001/0053334 A1 | 12/2001 | Chen et al. |
| 2001/0055765 A1 | 12/2001 | O'Keefe et al. |
| 2002/0001546 A1 | 1/2002 | Hunter et al. |
| 2002/0072096 A1 | 6/2002 | O'Keefe et al. |
| 2002/0110900 A1 | 8/2002 | Jovanovich et al. |
| 2002/0119578 A1 | 8/2002 | Zaffaroni et al. |
| 2002/0151040 A1 | 10/2002 | O'Keefe et al. |
| 2002/0155460 A1 | 10/2002 | Schellenberger et al. |
| 2002/0176804 A1 | 11/2002 | Strand et al. |
| 2003/0003036 A1 | 1/2003 | Rouleau et al. |
| 2003/0064507 A1 | 4/2003 | Gallagher et al. |
| 2003/0124716 A1 | 7/2003 | Hess et al. |
| 2004/0109793 A1 | 6/2004 | McNeely et al. |
| 2004/0141880 A1 | 7/2004 | Handler et al. |
| 2004/0171166 A1 | 9/2004 | Hunter |
| 2004/0191924 A1 | 9/2004 | Hunter et al. |
| 2005/0079105 A1 | 4/2005 | Hunter et al. |
| 2005/0118073 A1 | 6/2005 | Facer et al. |
| 2005/0148066 A1 | 7/2005 | O'Keefe et al. |
| 2005/0214173 A1 | 9/2005 | Facer et al. |
| 2005/0266582 A1 | 12/2005 | Modlin et al. |
| 2006/0194108 A1 | 8/2006 | Drews et al. |
| 2008/0108112 A1 | 5/2008 | O'Keefe et al. |

FOREIGN PATENT DOCUMENTS

| | | |
|---|---|---|
| EP | 0402888 | 12/1990 |
| EP | 0506993 | 10/1992 |
| EP | 0882593 | 12/1998 |
| EP | 1155742 A2 | 11/2001 |
| JP | 11061498 A | 3/1999 |
| JP | 200028623 A | 1/2000 |
| JP | 2000088863 | 3/2000 |
| JP | 2000287670 A | 10/2000 |
| JP | 2001083163 A | 3/2001 |
| JP | 2001211873 A | 8/2001 |
| JP | 2002189033 A | 7/2002 |
| JP | 2002283305 A | 10/2002 |
| JP | 2002335950 | 11/2002 |
| JP | 2002-27984 | 1/2004 |
| WO | 95/01559 | 1/1995 |
| WO | 95/11755 | 5/1995 |
| WO | 91/13335 | 9/1995 |
| WO | 97/15394 | 5/1997 |
| WO | 97/36167 | 10/1997 |
| WO | 97/37036 | 10/1997 |
| WO | 98/45406 | 10/1998 |
| WO | 98/47003 | 10/1998 |
| WO | 99/11373 | 3/1999 |
| WO | 99/19510 | 4/1999 |
| WO | 99/34920 | 7/1999 |
| WO | 99/39829 | 8/1999 |
| WO | 99/47922 | 9/1999 |
| WO | 99/52560 | 10/1999 |
| WO | 99/61152 | 12/1999 |
| WO | 00/01798 | 1/2000 |

(56) References Cited

FOREIGN PATENT DOCUMENTS

| WO | 00/51735 | 9/2000 |
|---|---|---|
| WO | 00/56456 | 9/2000 |
| WO | 01/61054 | 8/2001 |
| WO | 02/26394 | 4/2002 |
| WO | 02/30561 | 4/2002 |
| WO | 02/40158 | 5/2002 |
| WO | 02/5519 | 7/2002 |
| WO | 02/78834 | 10/2002 |
| WO | 02/87764 | 11/2002 |
| WO | 02/89982 | 11/2002 |
| WO | 03/02226 | 11/2003 |

OTHER PUBLICATIONS

Arndt et al., "A Rapid Genetic Screening System for Identifying Gene-Specific Suppresion Constructs for use in Human Cells,", *Nucleic Acids Research*, vol. 28, No. 6, pp. e15-i-viii (2000).
Ausubel et al., "Current Protocols in Molecular Biology", iii-xii (1987).
Birren, et al., "Genome Analysis Laboratory Manuel Series", *B. Birren, ed., Cold Spring Harbor Laboratory Press*. vols. 1-4, 1997-1999.
Brown, J.H. et al., "Charts for Counting Bacterial Colonies," *37 Am. J. Public Heath Nations Health*, vol. 37, pp. 206-207 (1947).
Cadus, *Cadus Pharmaceutical Corp1 1997 Annual Report*, 1-29, May 8, 1998.
Cheng, Tian-Lu et al., "Membrane-Tethered Proteins for Basic Research, Imaging and Therepy,"*Medical Research Reviews* (May 14, 2008).
Coleman, et al., "Phospholipid Synthesisi in Isolated Fat Cells,", *252 J. of Biological Chemistry*, vol. 252, pp. 3050-3056 (1977).
Cooper, Colin S. et al., "Applications of microarray technology in breast cancer research," *3(3) Breast Cancer Res.* 158-175 (2001).
Crameri, Andreas et al., "Improved Green Fluorescent Protein by Molecular Evolution Using DNA Shuffling", *Nature Biotechnology*, vol. 14, Mar. 1, 1996, 315-319.
De Macario, et al., *121 Methods in Ezymology*, 509-25 (1986).
De Macario, et al., "Adaption of the Slide Immuneozymatic Assay for Quantification of DNA Hybridization: SIA-DNA," *8 Biotechniques*, 210-217 (1990).
De Macario, et al., "Slide Immunoenzymatic Assay for Human IgE(SIA-IgE)," *90 J. Immunological Methods* 137-141 (1986).
Eckstein, et al., "Oligonucleotides and Analogues. A Practical Approach", *IRL Press*, 1991.
Erfle, H. et al., "Simultaneous loading of 200 sample lanes for DNA sequencing on vertical and horizontal, standard and ultrathin gels", vol. 25, No. 11, pp. 2229-2230, Oxford University Press, 1997.
Gait, "Oligonucleotide Synthesis—A Practical Approach", *IRL Press at Oxford University Press*, vii-xiii (1984).
Gillmor, S D. et al., "Low-Contact-Angle Polydimethyl Siloxane (PDMS) Membranes for Fabricating Micro-Bioarrays,", *Proc. 2d. Ann. Int'l IEEE-EMBS Spec Topic Conf. On Microtechnologies in Med. & Bio.* 51 (A. Dittmar, ed. 2002).
Green, ED, "Mapping Genomes", *vol. 4, Cold Spring Harbor Laboratory Press*, 1999.
Gregory, G L., "High-throughout gene expression analysis for drug-discovery", *5(2) Drug Discovery Today* 59-66 (Feb. 2000).
Hansson, et al., "Single-Step Recovery of a Secreted Recombinant Protein by Expanded Bed Adsorption", *Bio/Technology*, 1994, vol. 12, pp. 285-288.
Huhmer, Afr et al., "Noncontact Infrared-Mediated Thermocycling for Effective Polymerase Chain Reaction Amplification of DNA in Nanoliter Volumes," *72 Anal Chem.* 5507-5512 (2000).
Kanigan, Tanya et al., "Living Chips for Drug Discovery," *3926 Proc SPIE* 172-180 (2000).
Kricka, L J. et al., "Microchip PCR", *377 Analytical and Bioanalytical Chemistry*, 377, pp. 820-825 (2003).

Lee, Da-Sheeng et al., "A novel real-time PCR machine with a miniature spectrometer for fluorescence sensing in a micro liter volue glass capillary", *100 Sensors and Actuators B*, 401-410, 2004.
Lennon, G.G., Mapping Genomes, vol. 4, *Cold Spring Harbor Laboratory Press*, 1999.
Macbeath, G. et al., "Printing Proteins as Microarrays for High-Throughput Function Determination", Science 289, Sep. 2000, 1760-1763.
Maniatis, et al., "Molecular Cloning", *Cold springHarbor Laboratory*, 1982, 468-469.
Matsubara, Y. et al., "Microchamber Array Based DNA Quantification and Specific Sequence Detection from a Single Copy Via PCR in Nanoliter Volumes", *20 Biosensors and Bioelectronics* 1482-1490 (2005).
Matsubara, Y. et al., "On-chip Nanoliter-Volume Multiplex Taqman Polymerase Chain Reaction From a Single Copy Based on Counting Fluorescence Released from Microchambers,", *21 Anal Chem.*, 6434-6439 (2004).
Moerman, R. et al., "Miniaturized Electrospraying as a Technic for the Production of Microarrays of Reproducible Micrometer Sized Protein Spots, in Micro Total Analysis Systems 2000: *Proceedings of the u TAS 2000 Symposium*", (May 14-18, 2000).
Nagai, H et al., "Development of a Microchamber Array for Picoliter PCR", *73 Anal. Chemistry* 1043-1047 (2001).
Nagai, H. et al., "High-Throughput PCR in Silicon Based Microchamber Array,", *16 Biosensors & Bioelectronics* 1015-1019 (2001).
Patrick Adlecreutz & Bo Mattiass, ""Oxygen Supply to Immobilized Cells"", *16 Eur. J. Appl. Biotechnology 165-170 (1982)*.
PCT/US00/07140, International Search Report dated Jul. 19, 2000, 3 pgs.
Brazillian appl. No. PI0009164-2, Unfavorable Technical Opinion, Nov. 11, 2008.
Polokoff, et al., "Isolation of Somatic Cell Mutants Defective in the Biosynthesis of Phoshatidylethanolamine", *256 J. Biological Chemistry*, pp. 7687-7690 (1981).
Prescott, et al., "Microbiology", *Wm. C. Brown Publishers*, 1990, pp. 31; 114-116.
Rolls, et al., "A Visual Screen of GFP-Fusion Library Identifies a New Type of Nuclear Envelope Membrane Protein," *J. Cell Biol.*, vol. 146, No. 1, pp. 29-43 (1999).
Sambrook, et al., "Molecular Cloning—A Laboratory Manual", *Second Edition, Cold Springs Harbor Laboratory Press (1989)*, 2.53-2.54, 16.8-16.9, 16.20 and 16.22.
Sauter, A D. , "Nanoliters onto media: Use of Electric Induction," *American Laboratory 40-45* (Oct. 2001).
Shoffner, Mann A. et al., "Chip PCR. I. Surface passivation of microfabricated silicon-glass chips for PCR,", *24(2) Nucleic Acids Research* 375-379 (1996).
Sieweke, , "Direction of Transcription Factor Partners with a Yeast One Hybrid Screen," *Methods of Mol. Biol.*, vol. 130, pp. 59-77 (2000).
Singh-Gasson, et al., "Maskless fabrication of light-directed oligonucleotide microarrays using a digital Micromirror array", *Nature Biotechnology*, vol. 17, 1999, 974-978.
Smith, et al., "Dynamical Scaling of DNA Diffusion Coefficients", vol. 29, pp. 1372-1373, *Macromolecules*, 1996.
Steel, Adam et al., "The Flow-Thru Chip: A Three Dimensional Biochip Platform, in Microarray Biochip Technology", 87-117 *Mark Schena ed.*, 2000.
Taylor, Theresa B. et al., "Optimization of the Performance of the Polyermase Chain Reaction in Silicon-Based Microstructures", vol. 25, No. 15, *Nucleic Acids Research* pp. 3164-3168 (1997).
Thortstenson, et al., "Global Analysis of ATM Polymorphism Reveals Significant Functional Constraint", vol. 69, pp. 396-412, *Am J. Hum. Genet.*, 2001.
Vogelstein, et al., "Digital PCR", *Proc. Natl. Acad. Sci. USA*, vol. 96, Aug. 1999, 9236-9241.
Weast, Phd, Robert C. "CRC Handbook of Chemistry and Physics, Ed.", *65th Edition*, pp. F-20-F-35, 1984-1985.
Wittwer, "Current Protocols in Molecular Biology", vol. 1, *John Wiley & Sons, Inc.*, 1995.

(56) References Cited

OTHER PUBLICATIONS

Wittwer, C. T. et al., "Continous Fluorescence Monitoring of Rapid Cycle DNA Amplification", *Biotechniques, Informa Life Sciences Publishing, Westborough, MA.* vol. 22, No. 1, Jan. 1, 1997.

Wittwer, C.T. et al., "The LightCycler™: A Microvolume Multisample Fluorimeter with Rapid Temperature Control", *BioTechniques*, vol. 22 (1), Jan. 1997, 176-181.

Zhao, et al., *Combinatorial protein design: strategies for screening protein libraries, Current Opinion in structural biology* vol. 7, 1997, pp. 480-485.

Zhao, et al., "Directed Evolution Converts Subtilisin E into a Functional Equivalent of Thermitase,", *Protein Eng.*, vol. 12. No. 1, pp. 47-53 (1999).

Patrick Adlecreutz & Bo Mattiasson, Oxygen Supply to Immobilized Cells, *16 Eur. J. Appl. Biotechnology*, 165-170 (1982).

* cited by examiner

MULTI-THROUGH HOLE TESTING PLATE FOR HIGH THROUGHPUT SCREENING

CROSS-REFERENCE TO RELATED APPLICATIONS

The present application is a continuation of U.S. patent application Ser. No. 13/276,179, filed Oct. 18, 2011, which is a continuation of U.S. patent application Ser. No. 10/969,104, filed Oct. 20, 2004, which is a division of U.S. patent application Ser. No. 10/223,893, filed Aug. 20, 2002, which is a continuation of U.S. patent application Ser. No. 09/970,578, filed Oct. 4, 2001, which is a continuation of U.S. patent application Ser. No. 09/528,085, filed Mar. 17, 2000, which is a continuation-in-part of prior U.S. patent application Ser. No. 09/471,852 filed Dec. 23, 1999, which in turn is a continuation of U.S. patent application Ser. No. 09/272,122, filed Mar. 19, 1999, each of which are herein incorporated in their entireties by reference.

FIELD OF INVENTION

This invention is related generally to a testing apparatus and, more particularly, to a multi-through hole testing plate for high throughput screening.

BACKGROUND OF THE INVENTION

Prior testing apparatuses have consisted of a testing plate with a pair of opposing surfaces and a plurality of wells. The wells extend in from one of the opposing surfaces, but do not extend through to the other opposing surfaces. The wells are used to hold samples of solution to be analyzed.

Although these testing apparatuses work there are some problems. For example, the wells in these testing apparatuses are difficult to fill. Special delivery systems, such as large pipette systems, are needed to fill each of the wells with samples of solution. These special delivery systems are often expensive and difficult to operate. As a result, the overall cost of the testing procedure is increased.

Another problem with these prior testing apparatuses is with their construction. The bottom of the wells in these testing plates need to be transparent so that light can be transmitted through the samples during testing. However, the rest of the testing plate needs to be constructed of a non-transparent material. The construction of a testing apparatus with these characteristics is difficult and expensive.

Yet another problem with these prior testing apparatuses is with the operator locating a particular well in the testing apparatus. Typically, these testing apparatuses each include large numbers of wells which are equidistantly spaced apart. As a result, locating a particular well within the large number of wells is difficult.

Accordingly, there is a need for an improved testing apparatus for high throughput screening.

SUMMARY OF THE INVENTION

A method for holding samples in accordance with one embodiment of the present invention includes several steps. First, a testing plate with a pair of opposing surfaces and a plurality of holes is provided. Each of the holes extends from one of the opposing surfaces to the other one of the opposing surfaces. Next, at least one of the opposing surfaces of the testing plate is immersed in a solution to be analyzed. A portion of the solution enters openings for each of the holes in the immersed opposing surface and any gases in the holes escape through openings for each of the holes in the other opposing surface. Next, the testing plate is removed from the solution. Surface tension holds some of the solution in each of the holes. The opposing surfaces of the testing plate are then held above a supporting surface and the solution held in at least one of the holes is analyzed.

A method for identifying the location at least one sample of a solution in accordance with another embodiment of the present invention includes several steps. First, a testing plate with a pair of opposing surfaces and a plurality of holes is provided. Each of the holes in the testing plate extend from one of the opposing surfaces to the other one of the opposing surfaces. The holes in the plate are arranged in groups. Each of the groups comprises at least two rows and two columns of holes. Once a testing plate has been provided, solution is loaded into the holes and is then analyzed. Based on this analysis, the solution in at least one hole is identified for further study. The location of the identified hole is marked based upon the group in which the hole is found.

A method for screening a sample in accordance with another embodiment of the present invention includes several steps. First, a solution of the sample is prepared for screening. Next, a testing plate with a pair of opposing surfaces and a plurality of holes is provided. Each of the holes extends from one of the opposing surfaces to the other one of the opposing surfaces in the testing plate. Next, at least one of the opposing surfaces of the testing plate is immersed in a solution. A portion of the solution enters openings for each of the holes in the immersed opposing surface of the testing plate. Once the solution has enter into the holes, the testing plate is removed from the solution and the surface tension holds at least some of the solution in the holes. Next, the solution in one or more of the holes is analyzed.

An apparatus for holding samples of a solution with cells for analysis in accordance with another embodiment of the present invention includes a testing plate with a pair of opposing surfaces and a plurality of through holes. Each of the holes extends from an opening in one of the opposing surfaces in the testing plate to an opening in the other one of the opposing surfaces and is sized to hold a plurality of the cells. A portion of at least one of the opposing surfaces of the testing plate where the holes are located is recessed so that the openings in the testing plate are spaced in from the opposing surface.

An apparatus for holding samples for analysis in accordance with yet another embodiment of the present invention also includes a testing plate with a pair of opposing surfaces and a plurality of holes. Each of the holes extends from one of the opposing surfaces to the other one of the opposing surfaces. The holes are arranged in groups on the testing plate, where each of the groups comprises at least two rows and two columns of holes.

The method and apparatus for holding samples for analysis in accordance with the present invention provides a number of advantages. For example, the present invention simplifies testing procedures. The samples of solution to be analyzed can be loaded into the testing plate by simply dipping or flooding one of the surfaces of the testing plate into the solution. As a result, the present invention does not require the use of a separate delivery systems for loading solution into the wells on the testing plate.

The present invention also simplifies the construction of the testing apparatus. The testing apparatus merely needs one of the opposing surfaces of the testing apparatus to be spaced away by additional spacers or machined to create a recessed portion and then a plurality of holes need to be drilled through the plate in the recessed portion. Unlike prior testing apparatuses, the present invention does not require any special construction techniques to make the bottom of the wells transparent because the holes extend all of the way through the plate.

The present invention also permits an operator to more easily identify a particular hole filled with a sample for further analysis. Instead of spacing the holes equidistantly over the testing plate, the present invention arranges the holes in groups of at least two columns and two rows of holes and arranges the groups in sets of at least two or more. The groups are spaced further apart then the holes within each group and the sets of groups are spaced further apart then the groups are spaced apart. As a result, an operator can more easily identify a particular hole based upon which set, group, row, and column the hole is located in on the testing plate.

DETAILED DESCRIPTION

Figure 1:
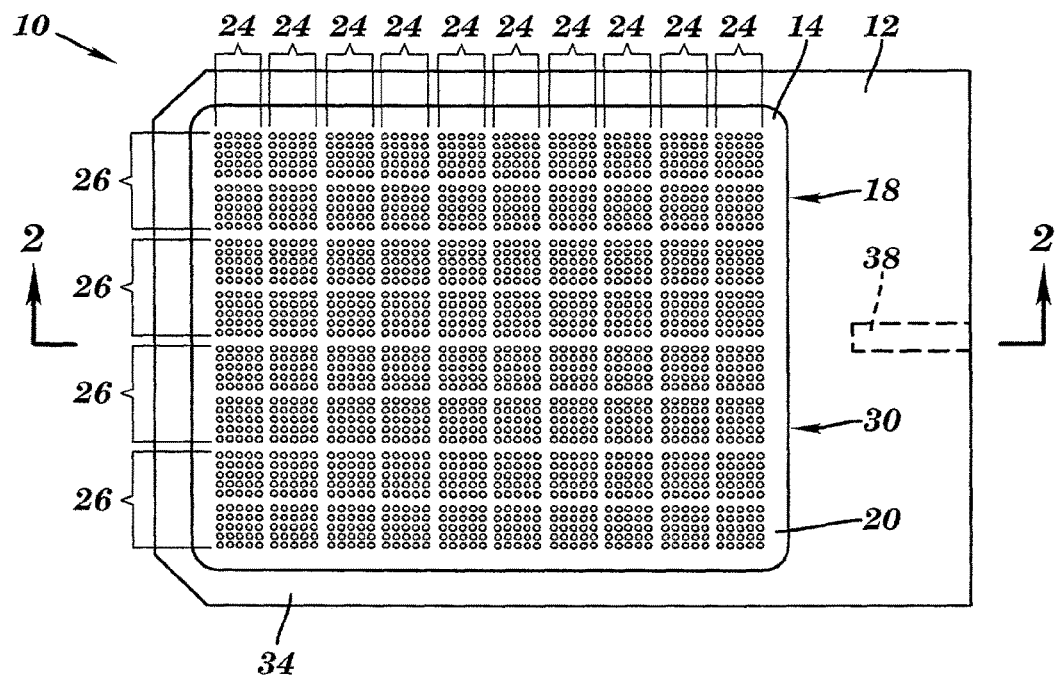
FIG. 1 is a top view of a multi-through hole testing plate in accordance with one embodiment of the present invention.
Figure 2:
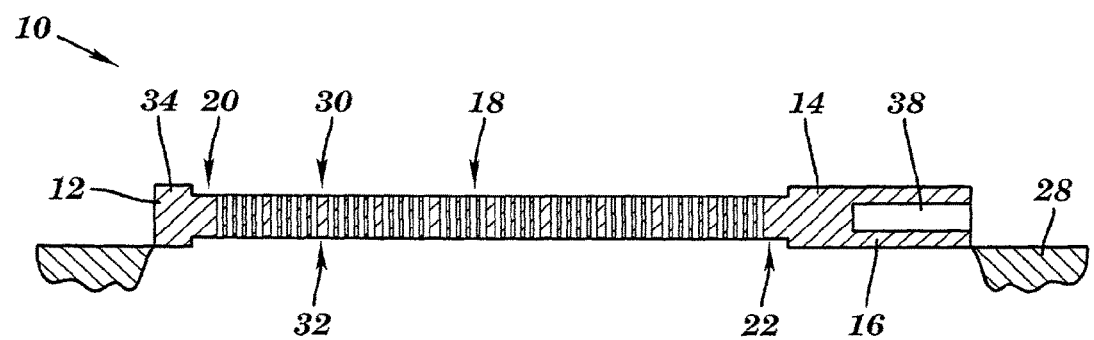
FIG. 2 is a cross-sectional view of the multi-through hole testing plate shown in FIG. 1 taken along lines 2-2.

A testing apparatus 10 in accordance with one embodiment of the present invention is illustrated in FIG. 1. The testing apparatus 10 includes a testing plate 12 with a pair of opposing surfaces 14 and 16 (surface 16 is shown in FIG. 2) and a plurality of through holes 18. The through holes 18 are located in recessed portions 20 and 22 on each side of the testing plate 12. The through holes 18 are also arranged in groups 24 of at least two columns and two rows of holes 18 and in sets 26 of two or more groups of holes 18. The testing apparatus 10 provides a number of advantages including simplifying the procedure for loading samples of solution S into the holes 18 in the testing apparatus 10, simplifying the construction of the testing apparatus 10, and making the identification of a particular hole 18 filled easier for an operator.

Referring to FIGS. 1 and 2, the testing apparatus 10 includes the testing plate 12 which in this particular embodiment is made of a non-transparent material, such as aluminum and polypropylene, although other types of materials, such as teflon, polystyrene, stainless steel, polyethylene, any metal or plastic, can be used. The testing plate 12 could also be made of transparent materials, such as glass or transparent plastic, when non-optical means are used for analysis, such as analyzing the materials blotted on membranes.

The testing plate 12 includes the pair of opposing surfaces 14 and 16. In this particular embodiment, the opposing surfaces 14 and 16 are substantially planar, except where the recessed portions 20 and 22 are located, although the surfaces 14 and 16 could have other relationships with respect to each other. Each of the opposing surfaces 14 and 16 includes one of the recessed portions 20 and 22 which are machined into the testing plate 12, although other techniques for forming the recessed portions 20 and 22, such as by molding or adding spaces, can be used. When either of the opposing surfaces 14 and 16 of the testing plate 12 rests on a supporting surface 28, the recessed portion 14 or 16 along with the plurality of holes 18 located in the recessed portion 14 or 16 are spaced away from the supporting surface 28. If openings 30 and 32 to the holes 18 contacted the supporting surface 28, then any solutions in the holes 18 would drain out of the holes 18. In this particular embodiment, a ridge 34 if formed in each of the opposing surfaces 14 and 16 by the recessed portions 20 and 22 which extends around the outer circumference of the testing plate 12. Although the holes 18 are spaced from the support surface 28 by a recessed portion 20 or 22 formed in the testing plate 12, the holes 18 can be spaced from the supporting surface 28 with other types of supporting structures, such as a bracket attached to the testing plate which supports the testing plate 12 and holes 18 above the supporting surface 28.

Figure 5:
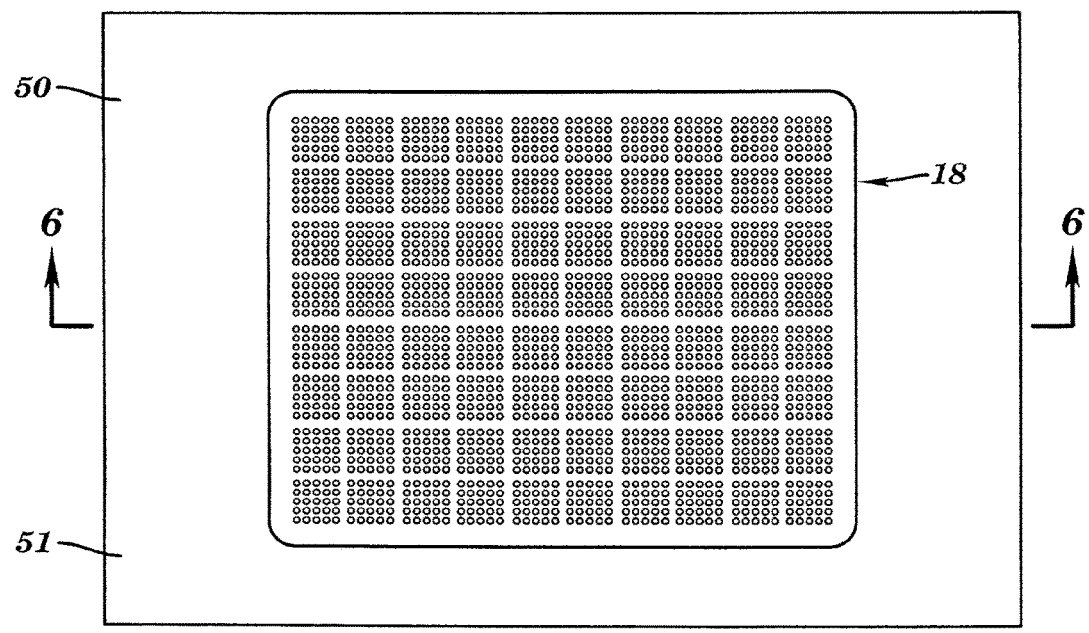
FIG. 5 is a top view of the multi-through hole testing plate in accordance with another embodiment of the present invention.
Figure 6:
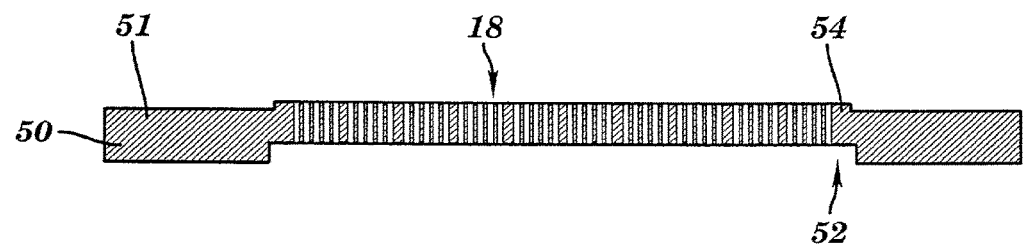
FIG. 6 is a cross-sectional view of the multi-through hole testing plate shown in FIG. 5 taking along the lines 6-6.

Referring to FIGS. 5 and 6, another testing apparatus 50 in accordance with one embodiment of the present invention is illustrated. The testing apparatus 50 is identical to the test apparatus 10 shown in FIGS. 1 and 2 except that the testing apparatus 50 does not include a pair of recessed portions. Instead, the testing apparatus 50 has a recessed portion 52 and a protruding portion 54. When the testing plate 51 is placed on a supporting surface, the recessed portion 52 must be facing the supporting surface so that the holes are spaced from the supporting surface. Although one example of the testing apparatus 50 is shown, the opposing surfaces of the testing plate 51 could have other configurations. For example, protruding portion 54 could be made flush with the upper surface of testing plate 51.

Figure 3:
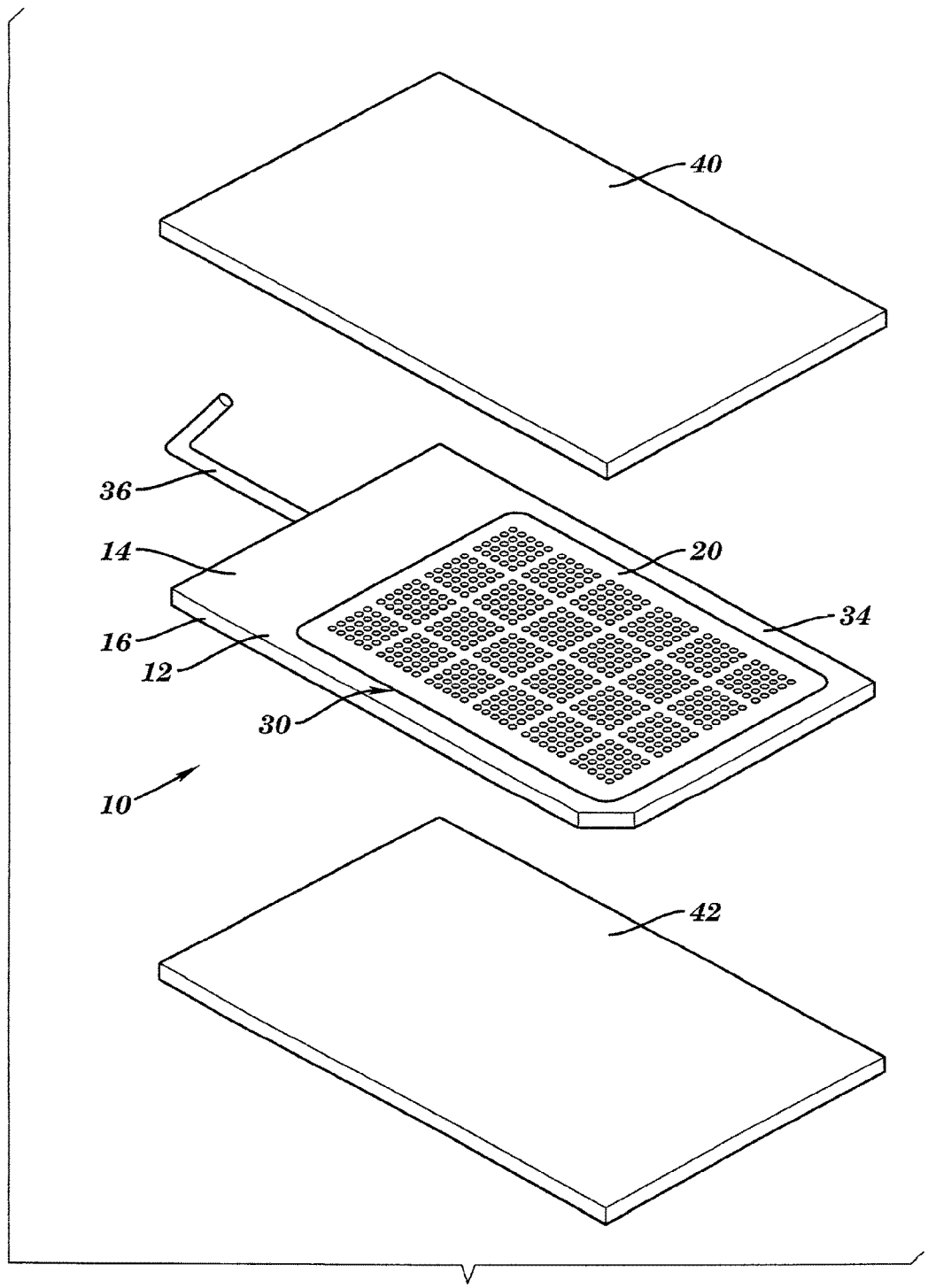
FIG. 3 is a perspective, exploded view of another multi-through hole testing plate in accordance with the present invention between a pair of evaporation plates.

Referring to FIGS. 1-3, the testing plate 12 also includes an optional handle 36 and an opening 38 on one side of the testing plate 12 to receive one end of the handle 36, although other techniques for connecting the handle 36 to the testing plate 12 can be used, such as connecting the handle 36 with bolts. The handle 36 extends out from the side of the testing plate 12 and is used to maneuver the testing plate 12 during loading and testing.

Figure 4:
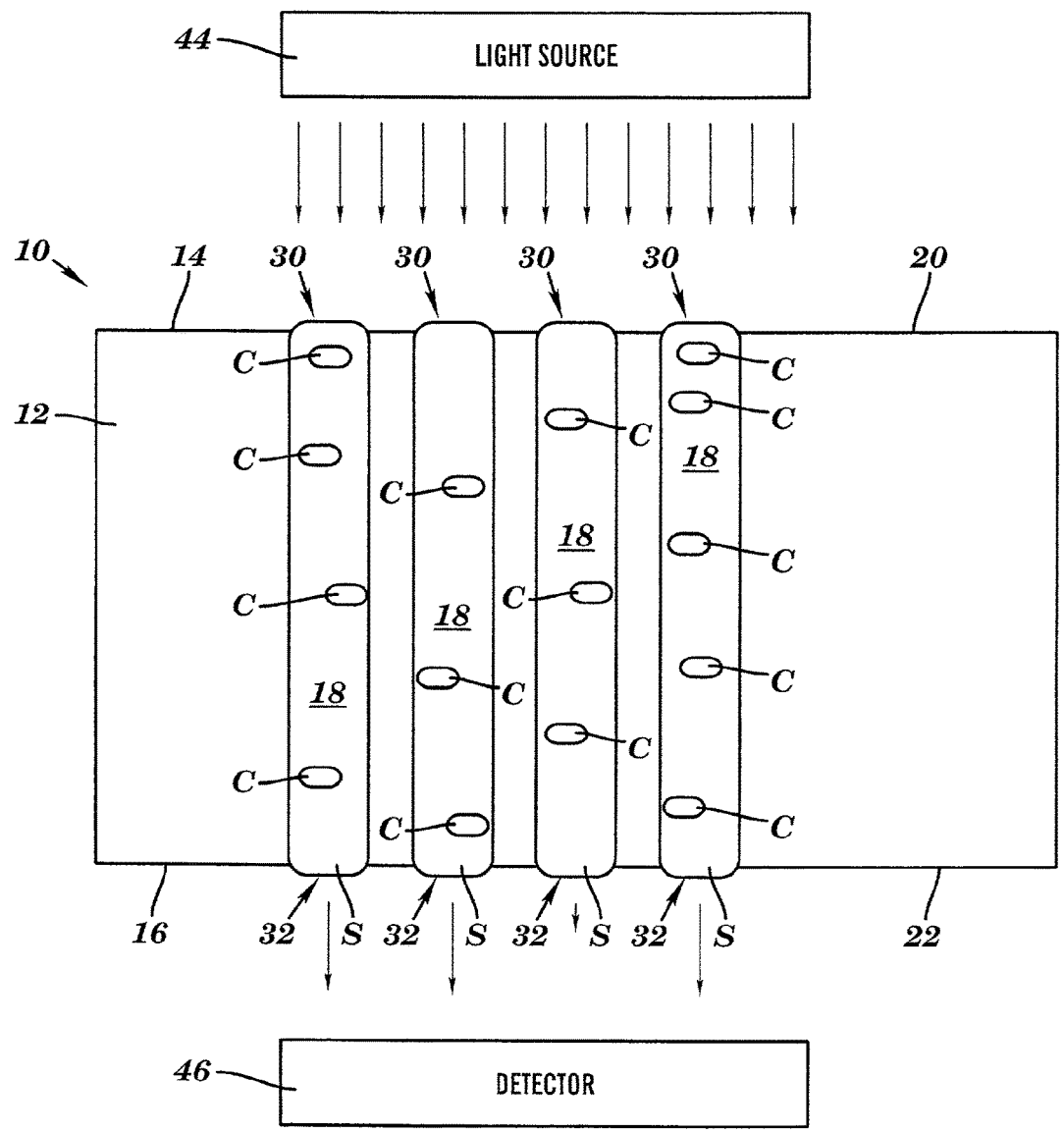
FIG. 4 is a block diagram of a testing apparatus with a multi-through hole testing plate in accordance with another embodiment of the present invention.

A plurality of through holes 18 are located in the testing plate 12. The holes 18 extend from openings 30 in the recessed portion 20 of one of the opposing surfaces 14 to openings 32 in the recessed portion 22 of the other opposing surface 16. In this particular embodiment, the holes 18 have a substantially cylindrical shape, although the holes 18 could have other shapes, such as a hexagonal cross-sectional shape or a cone shape. In this particular embodiment, each of the holes 18 has a diameter of about one millimeter and can hold about 5.5 microliters of solutions S and cells C, although the diameter, volume and number of cells C each hole 18 can hold can vary as needed or desired. The solution S along with cells C in the solution S are held in the holes 18 by surface tension as shown in FIG. 4. More specifically, the size of the holes 18 may need to change depending upon the solution S to be analyzed and that solution's surface tension properties. For example as understood by one of ordinary skill in the art, a buffer solution might have different surface tension properties than a culture media containing salt. There must be sufficient surface tension to keep the samples of solution S in the holes 18.

One of the advantages of the present invention is that the testing plate 12 is easy to manufacture. A plate having opposing surfaces can have an appropriate number of holes drilled there through. The plate can include one or more recessed portions 20, 22, and the through holes can pass through the recessed portion of the plate 12. Since the holes 18 extend all of the way through, there is no need for a transparent bottom in each hole 18. Light transmitted into the holes 18 will pass through during testing. With prior wells, the testing apparatus also needed to be non-transparent, but since the wells did not extend through the apparatus, the bottom of the wells needed to be made of a transparent material to permit light to pass through the sample for optical analysis. Constructing these prior testing apparatuses was difficult and expensive.

Referring to FIG. 1, the testing plate 12 has about two-thousand holes 18 which extend through from one opposing surface 14 to the other opposing surface 16, although the number of holes 18 can vary as needed or desired. To assist an operator in identifying a particular hole 18 in this particular embodiment the holes 18 are arranged in groups and sets of holes 18. Each group 24 contains at least two rows and two columns of holes 18 and each set 26 includes at least two rows and two columns of groups 24. In this particular embodiment, each group 24 of holes 18 has five rows and five columns of holes 18 and there are eighty groups 24 of twenty-five holes 18 in this example, although the number can vary as needed or desired. The holes 18 in this example are spaced about 1.5 mm apart between rows of holes 18 and between columns of holes 18 within each group 24, although this distance can vary and the spacing between rows of holes 18 and columns of holes 18 within each group 24 can be different as needed or desired. In this particular embodiment, each set of groups 24 includes two rows of groups 24 and ten rows of groups 24 and there are four sets 26 which contain twenty groups 24 of holes 18 each in this example, although the number can vary as needed or desired. The groups 24 within a set 26 in this example are spaced about 2.0 mm apart and the sets 26 of groups 24 of holes 18 in this example are spaced about 2.5 mm apart, although these distances can vary as needed or desired.

By arranging the holes 18 in sets 26 and groups 24, it is much easier for an operator to identify a particular hole 18 in the testing plate 12 and retrieve a particular sample. The sets 26 of holes 18 help the operator identify the general area of the hole 18 and then the groups 24 help the operator to begin to narrow down the location of the hole 18. The column and row of the hole 18 in each group 24 provides the precise location of the hole 18. The spacing between sets 26, groups 24, and rows and columns are different to make it visually easier for an operator to identify a particular hole 18. When the holes 18 are all spaced equidistantly apart, then it is more difficult to identify a particular hole 18 and it is easier for an operator to lose his/her place and select a sample from the wrong hole 18.

Figure 7:
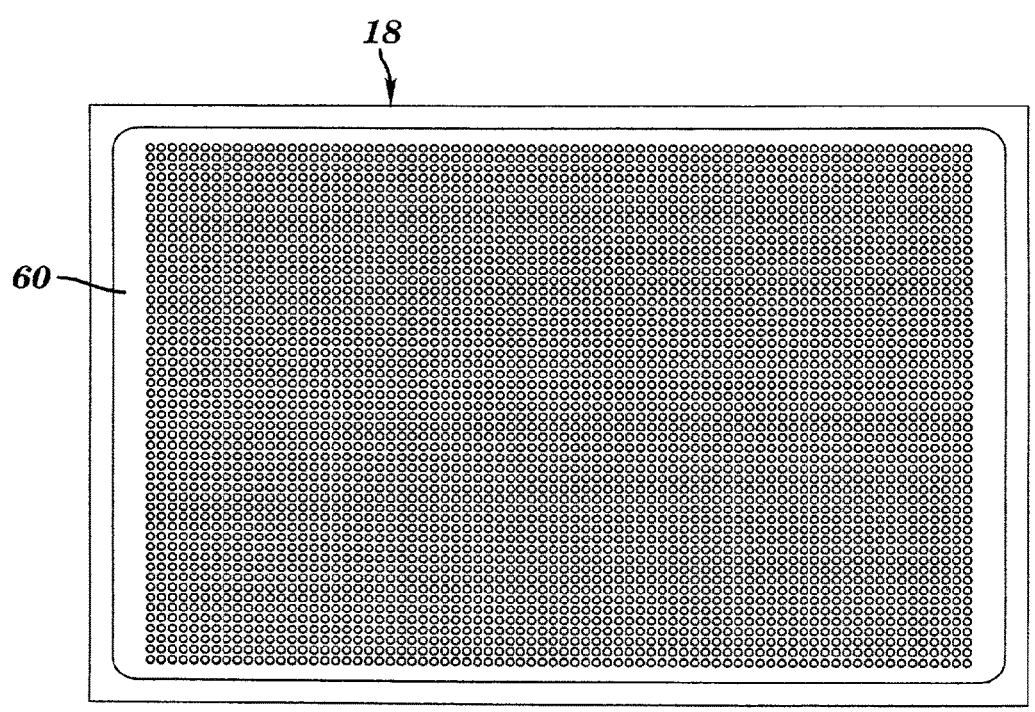
FIG. 7 is a top view of a multi-through hole testing plate in accordance with yet another embodiment of the present invention.

Although the holes 18 are arranged in groups 24 and sets 26 in testing apparatuses 10 and 50 to aid human operators, other arrangements for the holes 18 may also be used. For example, when the testing apparatuses are used by robotics, instead of human operators, the holes 18 can also be spaced equidistantly apart as shown in the embodiment of the testing apparatus 60 illustrated in FIG. 7. The testing apparatus 60 is identical to the testing apparatuses 10 and 50 described and illustrated earlier except for the that the holes 18 are equidistantly spaced apart.

Referring to FIG. 3, the testing apparatus 10 may also include a pair of optional evaporation plates 40 and 42. The evaporation plates 40 and 42 are each secured to the one of the opposing surfaces 14 and 16 of the testing plate 10. The evaporation plates 40 and 42 are secured to the testing plate 12 by bolts, clamps, or other mechanical means. When the evaporation plates 40 and 42 are secured to the testing plate 12 over the recessed portions 20 and 22, the recessed portions 20 and 22 in the opposing surfaces 14 and 16 of the testing plate 12 still space the openings 30 and 32 of the through holes 18 away from the evaporation plates 40 and 42. The evaporation plates 40 and 42 help to preserve the samples of solution S in the holes 18 in the testing plate 12 from evaporation and contamination.

Instead of a recessed portion in the plate 12, an assembly comprising the plate and evaporation plates can be provided with spacers between the testing plate and the evaporation plates to space the openings of the through holes away from the evaporation plates. The evaporation plates could be provided with recesses portions in addition to, or instead of, spacers between the testing plate and the evaporation plates. Any combination of recessed portions in the testing plate, recessed portions in the evaporation plates, or spacers can be used to provide the spacing between the openings of the through holes and the evaporation plates.

According to an embodiment of the present invention, stackable testing plates are provided which may or may not have evaporation plates in-between testing plates. The stackable testing plates may be provided with recessed portions or evaporation plates with recessed portions can be provided between a stacked testing plate. Any combination of recessed portions in the testing plates, recessed portions in the evaporation plates, or spacers can be used to provide a stack of testing plates wherein each testing plate is spaced from the surface of an adjacent testing plate, evaporation plate, or both.

One example of one application of the present invention will be discussed with reference to testing apparatus 10 shown in FIGS. 1-4. In this particular example, cells C are mutagenized using ultraviolet, chemical mutagenesis, or other mutagenesis technology. The cells C are grown to allow for segregation. Once the cells C have grown, the cells C are diluted to one cell C per ten microliters in a medium containing a fluorgenic or chromogenic substrate. For purposes of this example, the medium with the cells C is referred to as the solution S. As a result, the cells will be randomly distributed in the holes 18 and many of the holes 18 will contain one or more cells C.

Although one example of preparing the solution S and cells C is disclosed, other methods and techniques for preparing samples to be used with the testing apparatus 10 can be used as is readily understood by one of ordinary skill in the art.

Next, a testing plate 12 with a pair of opposing surfaces 14 and 16 and a plurality of holes 18 which extend from one of the opposing surfaces 14 to the other one of the opposing surfaces 16 is provided. At least one of the opposing surfaces 14 of the testing plate is immersed in the prepared solution S. The solution S enters openings 30 and 32 for each of the holes 18 in testing plate 12 and any gases in the holes 18 may escape through openings 30 and 32 at the opposite end of the holes 18. Alternatively, the testing plate 12 may be flooded with solution S so that the solution S enters through the top opening 30 to each hole 18.

One of the advantages of the present invention is the ease with which solution S can be loaded into each of the holes 18. As illustrated in the description above, all of the holes 18 in the testing plate 12 can be loaded with samples of solution S in a relatively short period of time and without any type of specialized solution delivery system. Prior testing apparatuses with wells required specialized solution delivery system, such as large pipette devices, to be able to load solution into each of the wells. These specialized solution delivery systems are difficult to use and are expensive.

Once the solution S has been drawn into the holes 18, the testing plate 12 is removed from the solution S. Surface tension holds the solution S in each of the holes 18. In this particular embodiment, each hole 18 has a diameter of about one millimeter and holds about 5.5 microliters of solution S and cells C as shown in FIG. 4, although the diameter and volume of each hole 18 can vary as needed or desired for the particular application. The handle 36 can be used to manipulate the position of the testing plate 12 during the above-described operations.

Once the testing plate 12 is removed from the solution S, the testing plate 12 can be placed on a supporting surface 28. Since the holes 18 are located in a recessed portion 22 of the testing plate 12, the openings 22 to the holes 18 are spaced from the supporting surface 28 so that any solution S being held by surface tension remains in the holes 18. A pair of evaporation plates 40 and 42 may be attached to the opposing surfaces 14 and 16 of the testing plate 12 to prevent the samples of solution S in the testing plate 12 from evaporating or becoming contaminated.

In this particular example, the testing plate 12 is then optionally incubated at a controlled temperature of about 37° C. and a humidity of about 70%, although the temperature and humidity will vary based upon the particular application. During the incubation, the cells multiply and produce a protein of interest (the cells could produce an enzyme, an antibody, or a metabolite which could be of interest). The ability of the protein, such as an enzyme, to hydrolyze a substrate is analyzed, such as by measurement of fluorogenic or chromogenic groups liberated by the hydrolysis.

Although one example of processing the samples of solution S in the testing plate 12 is disclosed, other methods and techniques for processing and analysis the samples can also be used and are know to those of ordinary skill in the art.

Next, in this particular example the samples of solution S with cells C in the holes 18 (as shown in FIG. 4) are tested using an image analyzer with a light source 44 and a detector 46 in this particular example. Light is transmitted from the light source 44 towards the openings 30 for the holes 18 in the testing plate 12 and through the solution S in the holes 18 of the testing plate 12. The detector 46 is positioned on the opposing side of the testing plate 12 and detects the light which has been transmitted through the solution S in the holes 18. Based upon the changes in the detected light from the transmitted light, information about the characteristics of the particular samples of solution S can be determined in a manner well known to those of ordinary skill in the art. In this particular example, the image analyzer is able to determine which holes 18 contain solution S with the highest concentration of converted substrate and consequently the highest amount of enzyme. The target in this case is to retrieve the cells C which produced the largest amount of enzyme. In a similar way, cells C which produced the largest amount of a protein or a chemical of interest could be identified.

Although one example of analyzing the samples of solution S in the testing plate 12 using optics is disclosed, other methods and techniques for analyzing the samples, such as non-optical methods, can also be used. For example, a plate containing samples of solution S with cells C could be blotted onto a membrane and used for performing Western blot analysis or alternatively, the samples S with cells C could be blotted onto substrate containing material whereby modification of the substrate is measured visually. As a result, when non-optical means are used to analyze the samples of solution in the testing plate 12, the testing plate 12 can be made of a transparent material.

Next, in this particular example the operator retrieves the samples of solution S which contain the highest concentration of converted substrate. The holes 18 with the solution S with the highest concentration of converted substrate can be identified and located based upon which set 26 of groups 24, which group 24, and which row and column within each group 24 each identified hole 18 is located. One of the advantages of the present invention is the arrangement of the holes in groups 24 and sets 26 which enables an operator to easily identify a particular hole 18 on the testing plate 12. Once the desired samples are retrieved, the operator can conduct further analysis on those samples in manners well known to those of ordinary skill in the art.

Although one example of retrieving one or more of the samples of solution S in the testing plate 12 is disclosed, other methods and techniques for retrieving samples can also be used. For example, if robotics are used to located and retrieve a particular sample, a different testing apparatus, such as testing apparatus 60 shown in FIG. 7, could be used. The robotics would not need the holes 18 to be arranged in groups 24 and sets 26 of holes 18, although such an arrangement may even aid the robotics in identifying and retrieving the desired sample.

According to some embodiments of the present invention, the testing plate is in the form of an assembly or substrate. For example, the plate can comprise a plurality of individual components which together make up an assembly having opposing surfaces and a plurality of through holes extending from one surface to the other. An example of the present invention wherein the testing plate comprises such an assembly is a plate made of a bundle of capillary tubes as shown in FIGS. 8 and 9.

Figure 8:
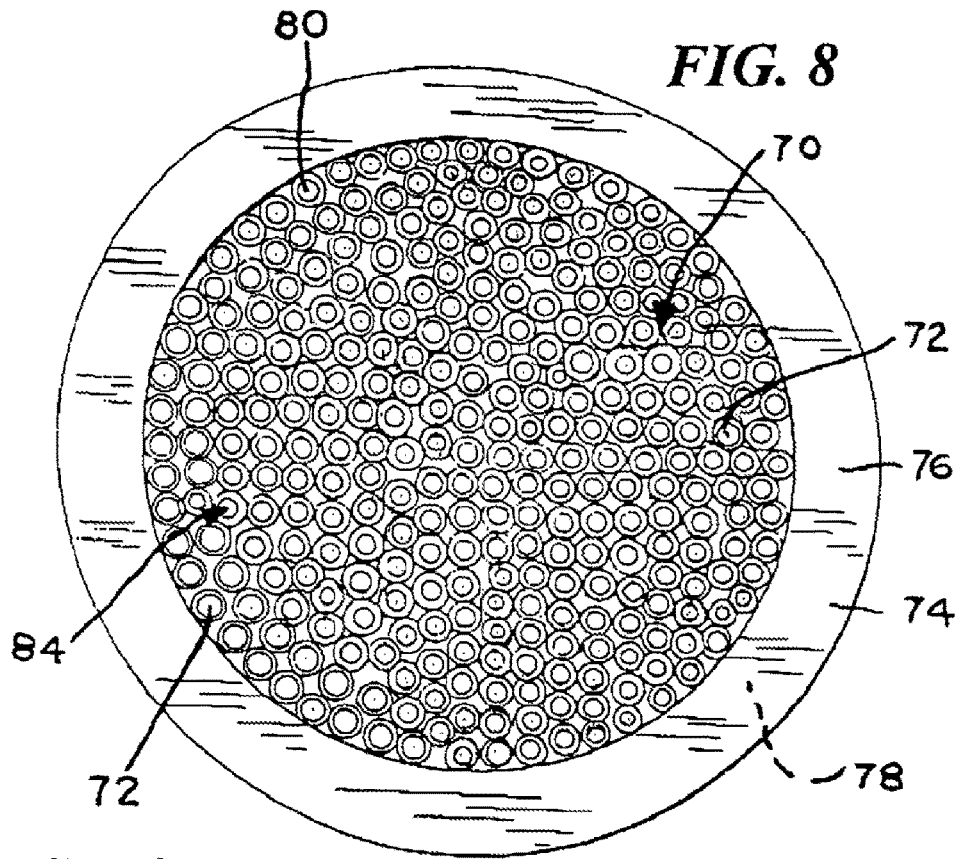
FIG. 8 is a top view of a testing plate assembly according to an embodiment of the present invention.
Figure 9:
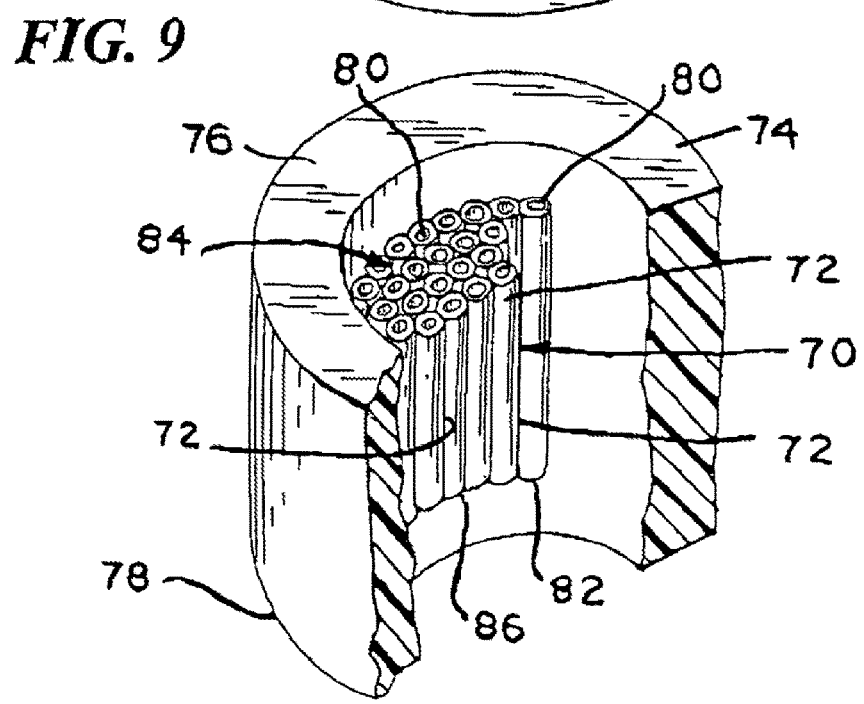
FIG. 9 is a perspective view of the assembly of FIG. 8 shown in partial cut-away.

As shown in FIGS. 8 and 9, a plate, substrate or assembly 70 comprises a bundle of capillary tubes 72 bound together by a band 74. The through holes of the assembly according to this embodiment are the longitudinally-extending holes through the center of each capillary tube. The band 74 may have opposing surfaces 76 and 78, each of which is substantially planar and substantially parallel to the other. The band can be made of metal, plastic, glass, rubber, elastomeric compound, or any other suitable material. Each capillary tube 72 has a first end 80 and a second end 82. The first ends 80 of the capillary tubes make up an opposing surface 84 of the substrate or assembly 70 and the second ends 82 of the capillary tubes 72 made up an opposing surface 86 of the substrate or assembly.

As can be seen in FIGS. 8 and 9, each capillary tube 72 of the bundle which makes up substrate or assembly 70 has a length between its first end 80 and its second end 82 which is at least two times greater than the average diameter of each tube. Preferably, the length of each tube is more than four times greater than the average diameter of each tube and is preferably many times greater than the average diameter. Each capillary tube may be, for example, in the form of a microcapillary tube or a hollow fiberoptic fiber.

The capillary tubes may be hollow cylindrical in shape or may have other rounded, oval, or polygonal cross-sections. The average diameter of each capillary tube preferably ranges from about 0.001 millimeter to about 1 millimeter, and the length of each tube preferably ranges from about 1 mm to about 1 cm. The dimensions of the capillary tubes are preferably such that each tube has the capacity to hold from about 0.0001 microliter to about 10 microliters of liquid sample, for example, about 5.5 microliters, although the diameters, lengths, and holding capacities of the capillary tubes may vary as needed or desired. According to some embodiments of the present invention, it is not necessary to have a band for holding the capillary tubes together in a bundle as the tubes may instead be fused or otherwise bonded, adhered, or maintained together in a bundle.

The number of capillary tubes of the embodiment in FIGS. 8 and 9 is preferably from about 100 to over 1,000 capillary tubes, for example, from about 500 to about 1,500. Preferably, the tubes are arranged in rows and preferably the rows are arranged in columns. Although in the embodiment shown in FIGS. 8 and 9 the bundle of capillary tubes 72 has a circular cross-section and the band 74 is ring shaped, other shapes of the bundle and band are also within the scope of the present invention. For example, a rectangular or square array of capillary tubes can be provided and surrounded by a band, and the band would also preferably be of rectangular or square shape. With rectangular or square-shaped arrays of capillary tubes, distinct columns and rows of capillary tubes can be easily identified, facilitating the identification of a single capillary tube within the array.

In embodiments such as the one shown in FIGS. 8 and 9, the band 74 surrounding the bundle of capillary tubes has a length between opposing surfaces 76 and 78 that is greater than the length between the opposing ends 80 and 82 of the capillary tubes. As a result, the banded assembly can be placed on a surface of, for example, an analytical device, without the ends of the capillary tubes touching the surface. In addition, the assemblies can be stacked without disturbing the capillary holding forces in the through holes.

The assembly shown in FIGS. 8 and 9, as with the plates of FIGS. 1-7, can be loaded or filled with a starting liquid sample to provide a plurality of samples, each constituting a portion of the starting liquid sample. Alternatively, the assembly can be loaded with more than one starting liquid sample, with each starting liquid sample filling at least one of the through holes. Herein, by "loaded" or "filled", what is meant is at least partially filled, but not necessarily fully filled. The through-holes can be loaded or filled, for example, by immersing the assembly or plate in a liquid sample, contacting at least one of the opposing surfaces of the assembly or plate with a liquid sample, or contacting the inner walls of the respective through holes with a liquid sample or with respective liquid samples.

Contact between a liquid sample and an opposing surface can be made by flooding, immersing, pipetting, dropping, pouring, or otherwise loading or at least partially filling a plurality of the capillary tubes or through holes such that capillary action pulls portions of the liquid sample into the respective capillary tubes or through holes. Upon removal or discontinued contact of the liquid sample with the assembly or plate, the opposing surfaces of the assembly or plate are preferably made free of liquid sample such that the portions of the sample that remain held within the respective capillary tubes are isolated from one another.

Automated filling devices can be used and are preferred if it is important that the respective liquid samples or liquid sample portions are to only contact the inner walls of the through holes and avoid contacting the opposing surfaces of the assembly.

According to embodiments of the present invention, a high throughput screening method is provided. The method can screen for at least one liquid sample that includes a target component or substance to be analyzed. Herein, the target component or substance to be analyzed may be referred to as an "analyte". The analyte may be, but is not necessarily, a biological sample. The analyte exhibits a detectable property or produces a detectable characteristic in the presence of or upon reaction with a marker compound or the like. For example, the analyte may itself exhibit a fluorescent property. After the liquid sample is at least partially filled into a plurality of the through holes, the portions of the liquid sample that contain the analyte can be detected by determining which of the through holes contains a sample portion that exhibits the fluorescent property.

In another example, the analyte itself does not exhibit a detectable property but may instead cause a marker component to exhibit a detectable property upon reaction with the marker component. According to such an embodiment, the through holes of the testing assembly can be pre-loaded or post-loaded with one or more marker components such that after loading the liquid sample into the plurality of through holes, the sample portions containing an analyte can react with the marker compound and thus enable the marker compound to exhibit a detectable property. In such a case, it is not the analyte itself that exhibits the detectable property, but rather the analyte is detected indirectly as the presence of the analyte causes the detectable property of the marker component which in turn is directly detected. In so doing, the methods of the present invention provide a way to partition and isolate analytes from an original liquid sample.

According to the high throughput screening method, portions of the liquid sample are loaded into a testing assembly having a pair of opposing surfaces and a plurality of through holes, with each of the through holes extending from one of the opposing surfaces to the other of the opposing surfaces. Loading preferably results in at least partially filling a plurality of the through holes with at least portions of the liquid sample, and surface tension holds the respective portions in the respective plurality of through holes. Multiple liquid samples can instead be loaded into respective through holes or into respective pluralities of through holes. The method then involves detecting which of the plurality of sample portions in the through holes exhibit the detectable property.

According to embodiments of the present invention, the high throughput screening assembly preferably comprises at least about 100 through holes, more preferably at least about 500 through holes, and according to some embodiments of the present invention, up to about 1,000,000 through holes. High throughput screening methods can be used in conjunction with these devices to test over 100,000,000 samples or sample portions per assembly per day.

The analyte to be screened may be, for example, a biological cell, a mixture of biological cells, a mutant cell, a secretable protein, an enzyme, a microorganism, a mixture of microorganisms, a contaminant, or combinations thereof. The analyte can be a population of random mutants of one or more organisms. If the analyte is a mixture of biological cells it could be a random sample isolated from a natural environment. The detectable property may be, for example, a fluorescence or adsorption property. Prior to filling the high throughput assembly, the liquid sample may be diluted with a suitable diluent to obtain a concentration of the analyte in the liquid sample such that when the sample is filled into the plurality of through holes, at least one of the analytes is introduced into from about one-quarter to about one-half of the plurality of through holes.

In some cases, it is possible to identify an organism with desirable properties even if the organism is introduced into a plurality of through holes as a mixture with other organisms. Under such conditions, the mixture of other organisms, e.g., mixture of biological cells, may be diluted prior to filling such that several organisms or cells will be introduced into each through hole. Using such a dilution technique, it is possible to detect the presence of an analyte. For example, it is possible to detect one particular mutant from a collection of many biological cells and mutants thereof despite having many cells from the mixture present in each through hole. Thus, for example, if a sample contains 1,000,000 cells and only one of them is a target mutant cell, referred to as the "analyte", and a testing plate having 10,000 through holes is employed, the sample can be diluted such that the 1,000,000 cells fill the through holes with sample portions wherein each portion contains about 100 cells. In cases where the detectable characteristic of the analyte is detectable despite the presence of many other cells within the same through hole, it is possible to isolate the analyte from 99.99% of the sample in a single assay.

The testing plates used in accordance with the present invention, including the plates of FIGS. 1-7 and the assemblies of FIGS. 8 and 9, can comprise hydrophilic materials or coatings, hydrophobic materials or coatings, or a combination thereof to facilitate loading of liquid sample portions into the through holes. For example, the opposing surfaces of the assembly can be made of, or treated with, a hydrophobic material such that liquid samples tend to be repelled from the surface except in areas immediately adjacent the through hole openings on the opposing surface. According to such an embodiment, liquid sample portions can be drawn into the through holes by capillary action without wetting-out onto the opposing surfaces of the plate. As a result, once the plate is loaded with and separated from a liquid sample no fluid communications are provided between individual through holes and contamination of the partitioned sample portions is minimized. According to some embodiments of the present invention, the through holes can include inner walls made of, or coated with, a hydrophilic material that can be easily wetted by an aqueous sample or medium. The entire inner walls of each through hole can be made of or treated with a hydrophilic material or only portions of the inner wall can be so made or treated. Plates having hydrophilic inner walls for the through holes and hydrophobic opposing surfaces provide excellent means to restrain, isolate, or limit the position of liquid samples in the through holes of the testing plate while keeping adjacent surface regions of the opposing surfaces substantially free of liquid sample.

According to some embodiments of the present invention, to facilitate the capillary reaction, it may be desirable to provide a hydrophilic material immediately adjacent the opening to each through hole on an opposing surface while maintaining or providing the remaining area of the opposing surface hydrophobic or non-hydrophilic. Either or both opposing surfaces of the testing plate can be made of or treated with hydrophobic, hydrophilic, or both materials as discussed above although if the through holes are to be loaded by an immersion technique, it is preferred that the opposing surface which will come in contact with the liquid sample is treated with or formed of a hydrophobic material except in areas immediately adjacent and preferably surrounding the through hole openings in the opposing surface.

Exemplary high throughput screening methods that can be used with the assemblies and other plates of the present invention include absorbance transcription assays, fluorescent transcription assays, fluorescent secreted enzyme assays, and microorganism screening assays. These and other suitable assays that can benefit from the plates and methods of the present invention are described, for example, in: Arndt et al., *A rapid genetic screening system for identifying gene-specific suppression constructs for use in human cells, Nucleic Acids Res.,* 28 (6): E15 (2000); Rolls et al., *A visual screen of a GFP-fusion library identifies a new type of nuclear envelope membrane protein, J. Cell Biol,* 146 (1): 29-44 (1999); Sieweke, *Detection of transcription factor partners with a yeast one hybrid screen, Methods Mol. Biol.,* 130: 59-77 (2000); and WO 97/37036, all of which are herein incorporated in their entireties by reference.

Having thus described the basic concept of the invention, it will be rather apparent to those skilled in the art that the foregoing detailed disclosure is intended to be presented by way of example only, and is not limiting. Various alternations, improvements, and modifications will occur and are intended to those skilled in the art, though not expressly stated herein. These alterations, improvements, and modifications are intended to be suggested hereby, and are within the spirit and scope of the invention. Accordingly, the invention is limited only by the following claims and equivalents thereto.

What is claimed is:

1. A system, comprising:
   a substrate comprising:
      a first surface facing in an upward direction;
      a first recessed portion recessed into the substrate from the first surface;
      an opposing second surface disposed below the first surface;
      a second recessed portion recessed into the substrate from the second surface; and
      a plurality of through holes extending from the first recessed portion to the second recessed portion, the through holes being sized to provide sufficient surface tension to hold respective portions of a liquid sample; and
   a first plate disposed over the first recessed portion, the first plate secured to the first surface of the substrate;
   wherein the first surface of the substrate spaces the first plate away from the through holes in a direction normal to the first surface.

2. A system, comprising:
   a first plate comprising:
      a first surface facing in an upward direction;
      an opposing second surface; and
      a plurality of through holes extending from the first surface to the second surface, the through holes being sized to provide sufficient surface tension to hold respective portions of a liquid sample;
   a second plate disposed over the through holes and secured to the first surface of the first plate; and
   a plurality of spacers that space the second plate away from the through holes in a direction normal to the first surface.

3. The system of claim 1, further comprising a liquid sample, the through holes holding respective portions of the sample liquid by surface tension.

4. The system of claim 1, a second plate disposed under the second recessed portion, the second plate secured to the second surface of the substrate, wherein the second surface of the substrate spaces the second plate away from the through holes in a direction normal to the second surface of the substrate.

5. The system of claim 4, further comprising a liquid sample, the through holes holding respective portions of the sample liquid by surface tension, wherein the first plate and the second plate are secured to the substrate so as to prevent evaporation of the sample liquid from the substrate.

6. The system of claim 1, wherein the first plate is secured to the first surface of the substrate by at least one of a clamp, a bolt, or a mechanical means.

7. The system of claim 1, further comprising a light source, a detector, and optics that together are configured to analyze a liquid sample disposed within the system.

8. The system of claim 2, further comprising a liquid sample, the through holes holding respective portions of the sample liquid by surface tension.

9. The system of claim 2, further comprising a third plate disposed under the through holes and secured to the second surface of the first plate, wherein the plurality of spacers space the third plate away from the through holes in a direction normal to the second surface.

10. The system of claim 9, further comprising a liquid sample, the through holes holding respective portions of the sample liquid by surface tension, wherein the second plate and the third plate are secured to the first plate so as to prevent evaporation of the sample liquid from the first plate.

11. The system of claim 2, wherein the second plate is secured to the first surface of the first plate by at least one of a clamp, a bolt, or a mechanical means.

12. The system of claim 2, further comprising a light source, a detector, and optics that together are configured to analyze a liquid sample disposed within the system.

13. A system, comprising:
a testing apparatus comprising:
 a first surface facing in an upward direction;
 a first recessed portion recessed into the testing plate from the first surface;
 an opposing second surface disposed below the first surface;
 a second recessed portion recessed into the testing plate from the second surface; and
 a plurality of spatially separated reaction regions configured to hold respective portions of a liquid sample;
a first plate disposed over the first recessed portion, the first plate secured to the first surface of the testing plate; and
wherein the first surface of the testing apparatus spaces the first plate away from the reaction regions in a direction normal to the first surface.

14. The system of claim 11, further comprising a liquid sample, the reaction regions holding respective portions of the sample liquid.

15. The system of claim 11, a second plate disposed under the second recessed portion, the second plate secured to the second surface of the testing apparatus, wherein the second surface of the testing apparatus spaces the second plate away from the reaction regions in a direction normal to the second surface of the testing apparatus.

16. The system of claim 15, further comprising a liquid sample, the reaction regions holding respective portions of the sample liquid, wherein the first plate and the second plate are secured to the testing apparatus so as to prevent evaporation of the sample liquid from the testing apparatus.

17. The system of claim 11, wherein the first plate is secured to the first surface of the testing apparatus by at least one of a clamp, a bolt, or a mechanical means.

18. The system of claim 11, further comprising a light source, a detector, and optics that together are configured to analyze a liquid sample disposed within the system.

* * * * *